United States Patent [19]
Benaron et al.

[11] Patent Number: 5,752,519
[45] Date of Patent: *May 19, 1998

[54] DEVICE AND METHOD FOR DETECTION, LOCALIZATION, AND CHARACTERIZATION OF INHOMOGENEITIES IN TURBID MEDIA

[76] Inventors: David A. Benaron, 25 Siesta Ct., Portola Valley, Calif. 94028; Boris Rubinsky, 1619 Sonoma Ave., Albany, Calif. 94707

[*] Notice: The term of this patent shall not extend beyond the expiration date of Pat. No. 5,746,210.

[21] Appl. No.: 725,239

[22] Filed: Oct. 4, 1996

Related U.S. Application Data

[63] Continuation of Ser. No. 24,278, Feb. 26, 1993, Pat. No. 5,283,794.

[51] Int. Cl.$^6$ ............................................. A61B 6/00
[52] U.S. Cl. ........................... 128/665; 128/633; 356/338
[58] Field of Search ................................. 128/664, 665, 128/633; 356/342, 237, 338; 250/574, 339, 341, 226

[56] References Cited

U.S. PATENT DOCUMENTS

| | | | |
|---|---|---|---|
| 4,948,974 | 8/1990 | Nelson et al. | 128/664 |
| 5,137,355 | 8/1992 | Barbour et al. | 356/342 |
| 5,203,339 | 4/1993 | Knüttel et al. | 128/665 |
| 5,293,210 | 3/1994 | Berndt | 356/39 |

*Primary Examiner*—Brian L. Casler
*Attorney, Agent, or Firm*—Flehr Hohbach Test Albritton & Herbert LLP

[57] ABSTRACT

The present invention provides a detection or imaging device and method that measures an effect upon the path traveled by a radiative wave through a medium where scattering of the radiative wave is strong, and uses this measured path effect to detect, localize, or characterize inhomogeneities in the medium, as well as of the medium itself, over time or space. In this embodiment, a radiative source (43), temporally modulated or intensity quantitated, is emitted into the medium (47). A detector (48) records radiative effects detected after travel through said medium, and the detected signal is measured for a path effect (45). Based upon one or more of these path effects, such as the distance the latest arriving photons have traveled, a quantifiable parameter of the medium is determined (49). This parameter can be the location, distance, speed, or other characteristic of the medium or inhomogeneity. Measurement over space provides additional information as to spatial distribution; measurement over time provides information as to temporal changes in the medium. The device has application in medical and industrial imaging, detection, and localization of objects and other inhomogeneities, as well as characterization of the medium itself, in media which highly scatters radiative waves emitted into the medium.

17 Claims, 14 Drawing Sheets

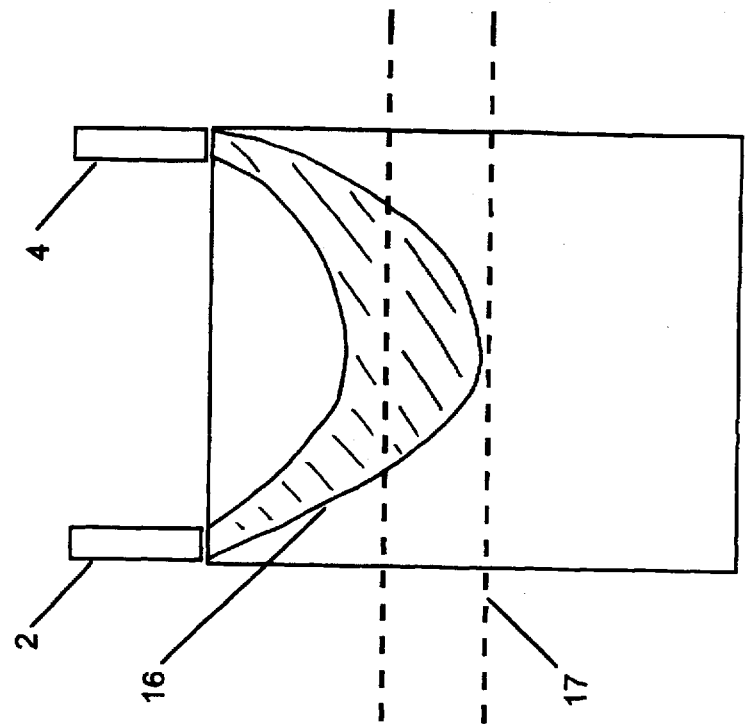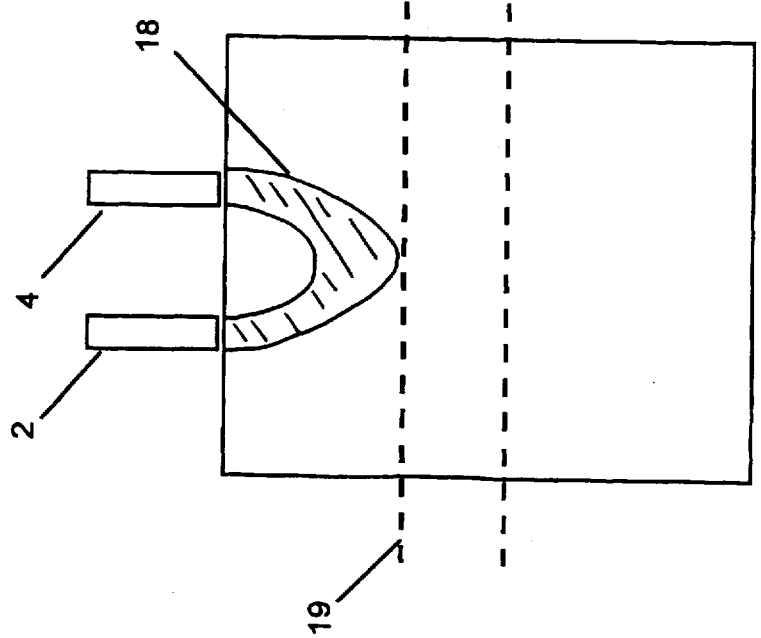
FIG. 3B
FIG. 3A

Optical Distance By Detector vs. Distance of Object 25

| Detector | Distance | | | | | | | | | |
|---|---|---|---|---|---|---|---|---|---|---|
| | 100mm | 40mm | 30mm | 20mm | 10mm | 10mm | 10mm | 10mm | 10mm | 1mm |
| 24A | 10mm | 10mm | 10mm | 10mm | 10mm | 10mm | 20mm | 20mm | 20mm | 10mm |
| 24B | 20mm | 20mm | 20mm | 20mm | 20mm | 20mm | 20mm | 30mm | 20mm | 20mm |
| 24C | 30mm | 30mm | 30mm | 28mm | 20mm | 20mm | 30mm | 38mm | 38mm | 38mm |
| 24D | 40mm | 38mm | 30mm | 30mm | 40mm | 40mm | 45mm | 50mm | 50mm | 50mm |
| 24N | 50mm | 45mm | 40mm | 40mm | 50mm | 53mm | 57mm | | | |

Path Ratio by Detector vs. Distance of Object 25

| Detector | Distance | | | | |
|---|---|---|---|---|---|
| | 100mm 40mm | 30mm | 20mm | 10mm | Touching |
| 24A | 5.00 5.00 | 5.00 | 5.00 | 5.00 | 5.00 |
| 24B | 5.00 5.00 | 5.00 | 5.00 | 5.00 | 5.00 |
| 24C | 5.00 5.00 | 4.66 | 3.66 | 5.00 | 6.33 |
| 24D | 5.00 4.75 | 3.75 | 5.00 | 5.62 | 6.25 |
| 24N | 5.00 4.50 | 4.00 | 5.00 | 5.30 | 5.70 |

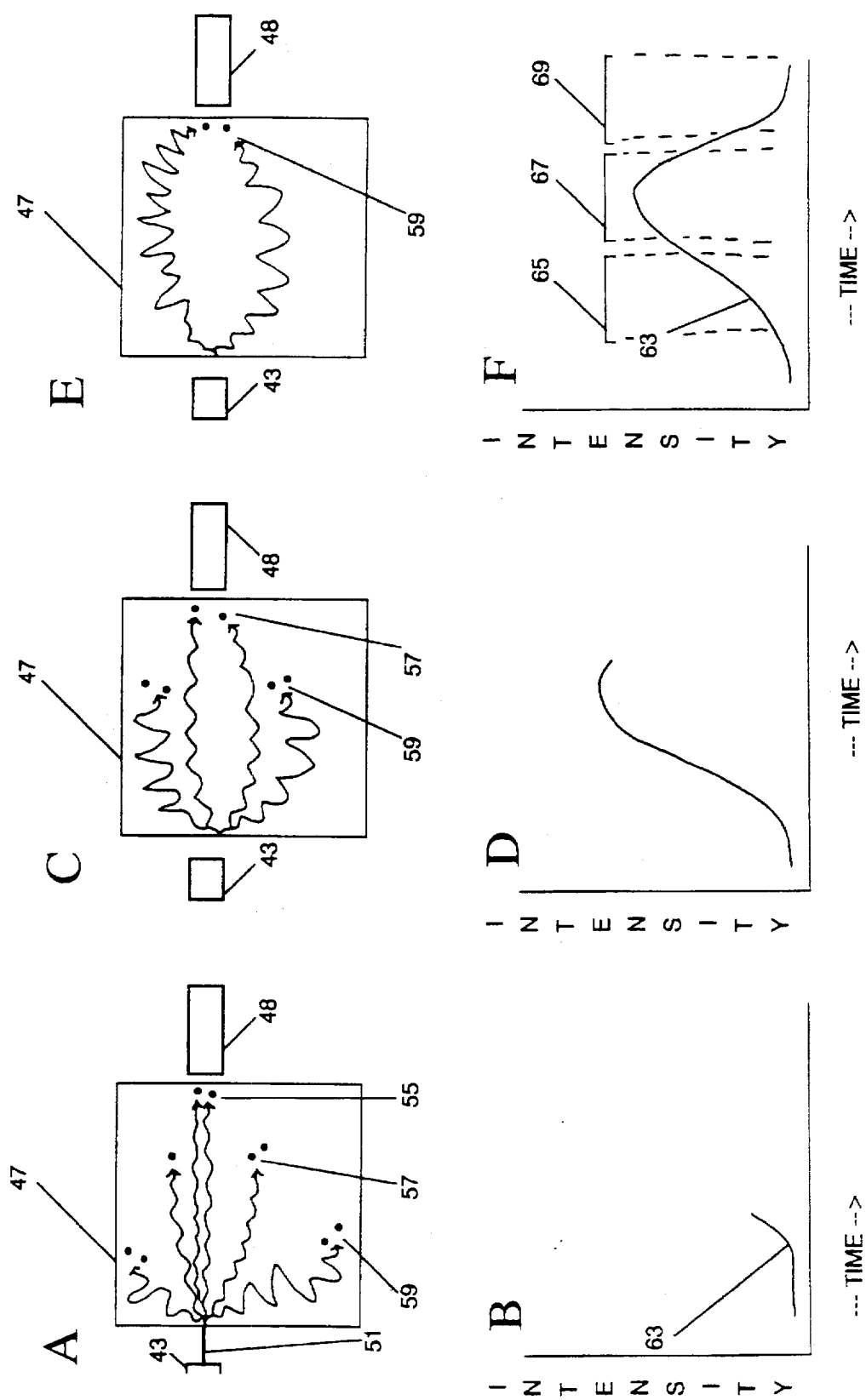

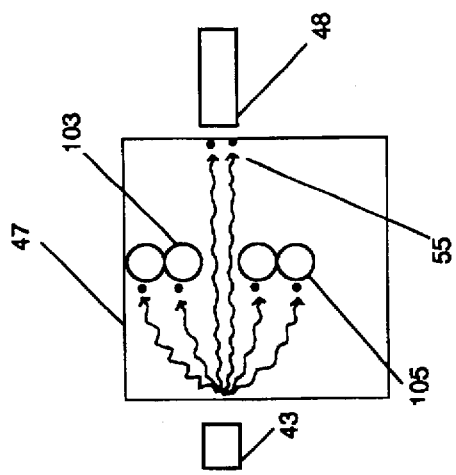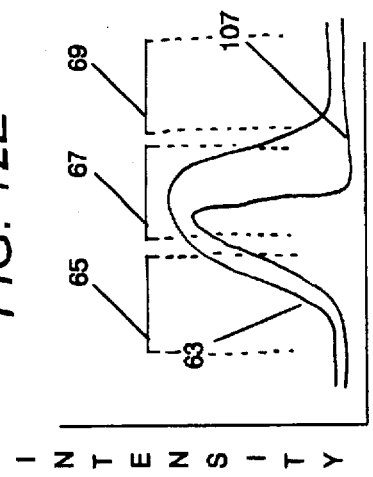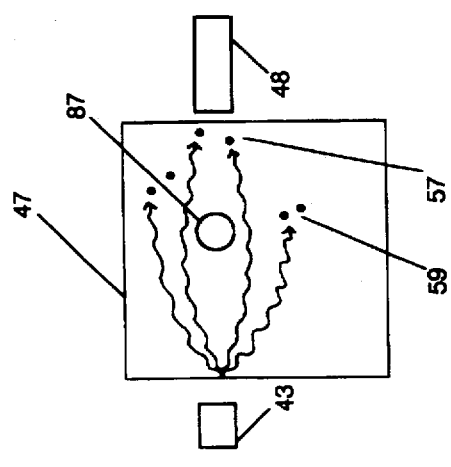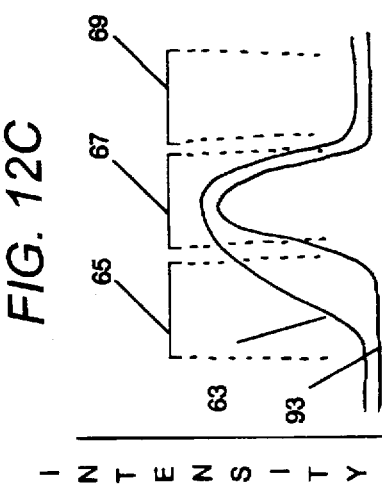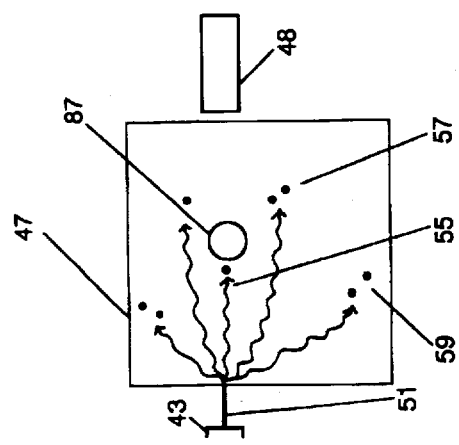

DEVICE AND METHOD FOR DETECTION, LOCALIZATION, AND CHARACTERIZATION OF INHOMOGENEITIES IN TURBID MEDIA

This is a continuation of application Ser. No. 08/024,278 filed Feb. 26, 1993, now U.S. Pat. No. 5,283,794.

FIELD OF THE INVENTION

The present invention relates to a device and method for detecting, localizing, and characterizing inhomogeneities in a turbid medium, and more particularly relates to an radiative device and method, in this embodiment an optical device and method, for measuring information regarding the course of a radiative wave taken through a medium between illumination and detection, and using said information to detect, localize, or characterize inhomogeneities in said medium.

REFERENCES CITED

A list of references cited herein is provided to assist in the study of this application, as follows:

| U.S. PAT. NOS. CITED | | | |
|---|---|---|---|
| 4,509,368 | 4/1985 | Whiting et al. | 73/624 |
| 4,765,736 | 8/1988 | Gallagher et al. | 356/300 |
| 4,773,097 | 9/1988 | Suzaki et al. | 382/6 |
| 4,805,623 | 2/1989 | Jöbsis | 128/633 |
| 4,872,187 | 10/1989 | Nakahata et al. | 378/4 |
| 4,910,404 | 3/1990 | Cho et al. | 250/358 |
| 5,119,815 | 6/1992 | Chance | 128/633 |

OTHER PUBLICATIONS

Benaron, D. A., et al., "2-D and 3-D Images of Thick Tissue Using Time-Constrained Time-of-Flight (tc-TOFA) Spectrophotometry." SPIE 1641:3545 (1992).

Benaron, D. A., et al. (1992). "Imaging (NIRI) and quantitation (NIRS) in tissue using time-resolved spectrophotometry," SPIE 1888, in press (1993).

Benaron D. A. and Stevenson D. K., "Optical Time-of-Flight Imaging of Biologic Media," Science, in press, (1993).

BACKGROUND OF THE INVENTION

In many types of radiation scattering media, such as those that appear turbid because they scatter light, it is important to detect or locate in the medium the presence of changes in state (such as freezing), changes in environment (such as the proximity of another object), or disturbances of homogeneity (such as in the presence of a tumor in tissue). Whichever type of radiative wave is used to attempt imaging, such as electromagnetic, electrical, sound, or pressure, scattering can be a major barrier to effective imaging. In contrast, in non-scattering media, such as pure water measured using visible light, most imaging techniques function adequately as the radiation travel is linear. For example, in pure liquid water, localization of an inhomogeneity can be performed visually. However, if the medium is not clear, such as in turbid water or human tissue (which is composed primarily of water), then standard techniques, such as those taught by Suzaki et al. (U.S. Pat. No. 4,773,097) to image biological material using standard optics, will fail. Such standard optical techniques do not work when the image received is blurred substantially by the presence of scattered light. Similarly, standard methods for detecting radiative sound or pressure waves, do not function correctly if substantial scattering of the signal is present, and therefore the assumptions of linear radiative travel are no longer valid.

This problem of scattering destroying images and interfering with the ability to detect inhomogeneities in a medium is also present when using other types of radiation for the imaging or detection. While Nakahata (U.S. Pat. No. 4,872,187) teaches a method of tomography that allows imaging within scattering media such as human tissue using x-rays, the technique depends upon the absorption of radiation, and does not correct for the effect of the path taken through the medium due to scattering. Thus, this technique could fail in highly x-ray scattering media. Also, in many cases a tomographic x-ray approach is too expensive or not appropriate. For example, x-rays are carcinogenic, and cannot be used on a continuous basis such as visible or near-infrared light can. Similarly, ultrasound, as taught in tomographic mode by Whiting et al. (U.S. Pat. No. 4,509,368), while able to be used to image in a turbid medium such as tissue, is not designed to function well when the scattering of radiation is large and no clear echo is received from the object to be imaged. Therefore, scattering remains a major barrier to effective detection and imaging.

There have been some attempts in the art to correct for the effects of scattering in order to image or detect objects. These attempts have used various techniques, each of which differs in substantial ways from those taught in the present invention. For example, Jobsis (U.S. Pat. No. 4,805,623) teaches a method of using light to measure concentration, but this concentration is merely quantitated, but not localized, and the detection requires the presence of first and second substances, one of which must be dilute. In addition, Jobsis' technique requires a measurement of both an intensity as well as an "apparent effective pathlength," which is ill defined. Chance (U.S. Pat. No. 5,119,815) also studied the manner in which light travels through tissue, and uses a rate of decay of intensity to determine characteristics of tissue. These characteristics are not dependent upon a path effect, and are not used for detection or imaging. Cho and Kanda (U.S. Pat. No. 4,910,404) teach a method of optical tomography, which would allow localization of objects, but relies upon the use of a second harmonic and various structural means not necessary, and not found in, the present invention, which relies upon a function of path effect alone to construct images. Gallagher et al. (U.S. Pat. No. 4,765,736) teach a method of emitting modulated light into a medium, but measure absorbance directly, rather than measuring a path effect, for the purpose of determining spectral characteristics of substances. The use of path effect is not disclosed, not are approaches to make such determinations spatial. Benaron (1992, 1993A, 1993B) had earlier shown that there is information contained in the manner that light travels through tissue, but the use of a path effect alone to perform imaging, as opposed to a combined path and absorbance effect, has not yet been disclosed (such an approach, however, is disclosed in the 1993A and 1993B articles, unpublished and in press).

In the current art, therefore, all known methods, and the obvious improvements that can be made upon these for the purposes of detecting and localizing inhomogeneities, could fail, and may be expected to fail, in highly scattering media. What is needed, and not found in the current art, is a device capable of detecting inhomogeneities in a radiation scattering medium, and perhaps localizing and characterizing these features, in a noninvasive manner using path effects in detected radiative waves, where such waves may be electromagnetic, electrical, pressure, sound, or of another type in nature. Such an approach has now been developed by Benaron, and will now be described.

SUMMARY OF THE PRESENT INVENTION

A salient feature of the present invention is an incorporation of the observation that radiation, while both being scattered and absorbed by scattering media, can be made to penetrate such scattering media such as human tissue, the atmosphere, or even a suitcase in an airport scanner, and then be detected upon reemergence from that material in order to allow quantitation of characteristics of inhomogeneities in the interior of the medium, imaging of such inhomogeneities, or merely detection of such inhomogeneities, or even characterization of the media itself.

Accordingly, an object of the present invention is to provide a noninvasive method for detecting the presence of an object or inhomogeneity in a medium using an optical path effect, whether to merely detect such change, to quantify such change, or to localize the change.

A second object is to provide a noninvasive method for optically detecting the presence of a change in the state of a medium using an optical path effect, whether to merely detect such change, to quantify such change, or to localize the change.

A third object is that such detection can be performed using various types of scattered radiative waves, whether the radiative wave is electromagnetic, electrical, pressure, sound, or of other types of waves known to travel through scattering media.

Additional objects of the invention are to detect such inhomogeneity, or a change in such, either by a direct measurement of a change in the paths taken by the radiating wave through the medium, or to detect such effects by measurement of an effect caused by such changes in path, such as the decreased absorption seen when photons travel, on average, less far through a radiation attenuating medium due to the presence of an object which blocks the farthest traveling scattered waves from reaching a detector. Such a measurement of a path effect, rather than path itself, may be more economical to achieve than direct measurement of path itself.

Another object is that this technique is not limited to the imaging of a medium from the outside (e.g., such as is commonly done in computed x-ray tomography), but also may be used to allow a probe to measure its surrounding medium, such as if a needle is to be inserted into a tumor, to allow sizing and measurement of said tumor from the inside, or if an underwater probe is to take note of objects nearby, such as rocks, when the water is cloudy, to allow better guidance. Thus, such an approach can be used both to detect changes within a medium, as well as around a probe submerged in a medium that comprises the environment of the detection apparatus.

Another object is that this data can be enhanced by collection over time. In many medical applications, the value of a measurement is enhanced by determination of temporal characteristics. For example, the detection of an enlarging bleed in head tissue holds a different significance than the detection of a stable, but otherwise similar, bleed. In underwater applications, the ability to detect moving nearby objects may also be important.

A final object is that the detection, localization, or imaging information can be presented to the user in a number of ways, such as an image of object location or even an image of characteristics of the medium such as absorbance, in such a manner as to allow the user to gain an incremental understanding of the presence or location of inhomogeneities in the medium, or even an understanding of characteristics of the medium itself.

The breadth of uses and advantages of the present invention are best understood by example, and by a detailed explanation of the workings of a constructed apparatus, now in operation. These and other advantages of the invention will become apparent when viewed in light of accompanying drawings, examples, and detailed description.

BRIEF DESCRIPTION OF THE DRAWINGS

The following description of the drawings is provided as an aid to the examiner:

FIGS. 3A and 3B illustrate changes in depth of optical penetration with changes in emitter-detector spacing

FIGS. 11A, 11B, 11C, 11D, 11E, and 11F illustrate a time-of-flight collection of scattered pulsed light;

FIGS. 12A, 12B, 12C, 12D, 12E, and 12F illustrate the effect of an object in turbid media upon time-of-flight curves;

LIST OF THE REFERENCE NUMERALS

Figure 1:
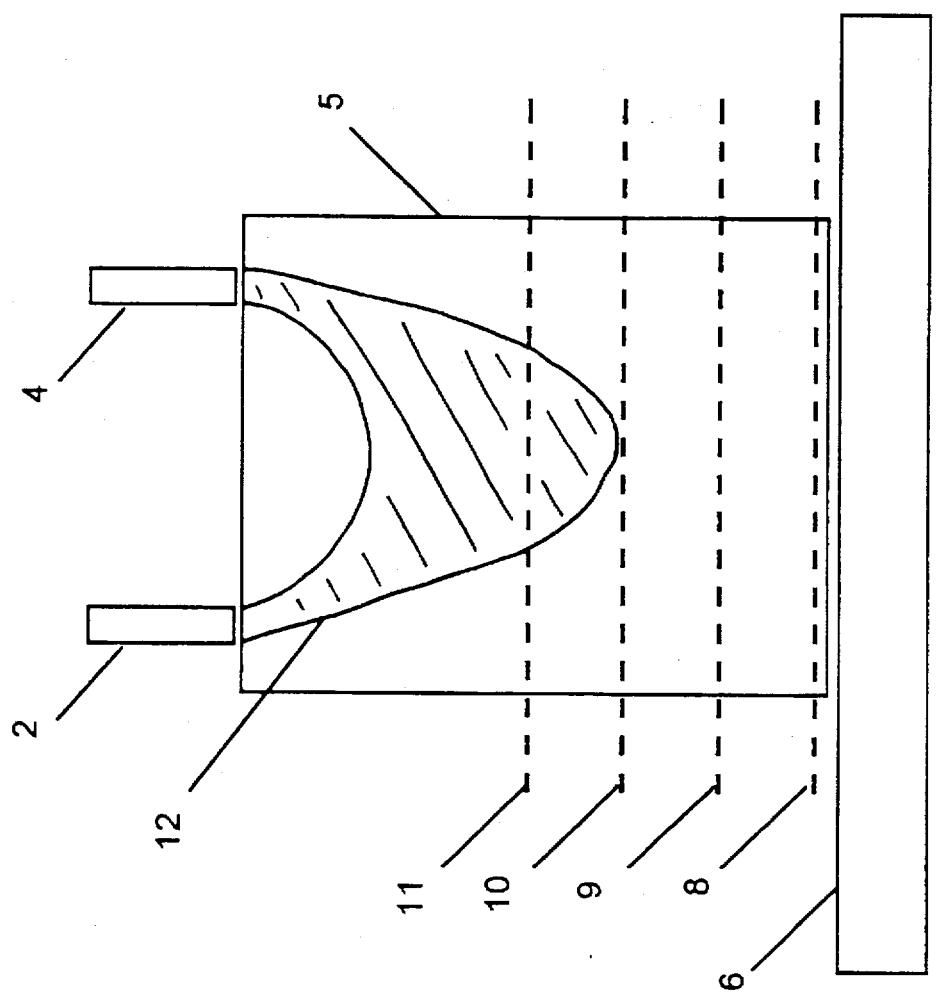
FIG. 1 illustrates the use of the apparatus to detect and localize a freezing interface in freezing tissue.

A complete list of reference numerals is provided to assist in the study of the description and figures, as follows:

| | |
|---|---|
| 2 | emitter on tissue cube |
| 4 | detector on tissue cube |
| 5 | tissue sample |
| 6 | thermal heating/cooling plate |
| 8 | interface 35 mm from probes |
| 9 | interface 30 mm from probes |
| 10 | interface 25 mm from probes |
| 11 | interface 20 mm from probes |
| 12 | banana shaped photon path distribution |
| 13A | average photon path length calibration curve |
| 13B | first arriving photon path length curve |
| 14 | mark where path length changes appear |
| 15 | mark where tissue fully frozen |
| 16 | shallow traveling banana-shaped region |
| 17 | maximum shallow banana photon depth |
| 18 | deep traveling banana-shaped region |

-continued

| | |
|---|---|
| 19 | maximum deep banana photon depth |
| 20 | absorbance path-effect calibration curve |
| 21A-N | detector array |
| 22A | skin interface |
| 22B | freezing interface |
| 22C | sensing capsule |
| 23A-N | emitter array |
| 24A-N | detector array |
| 25 | object to be detected |
| 26A-N | marks on scalp from right to left ear |
| 27A-N | marks on right scalp from front to back |
| 28A-N | marks on left scalp from front to back |
| 29L | Fluid in left brain |
| 29R | Fluid in right brain |
| 31 | control unit |
| 32 | cable |
| 33 | remote processor |
| 34A | sensor source |
| 34B | sensor detector |
| 35 | cable |
| 36A | power switch |
| 36B-C | adjust |
| 37 | display panel |
| 38 | detachable plug |
| 40 | controller |
| 41 | pulse generator |
| 43 | light emitter(s) |
| 45 | time-of-flight measurer |
| 46 | multichannel recorder |
| 47 | study medium |
| 48 | light detector(s) |
| 49 | parameter calculator |
| 50 | output device |
| 51 | light pulse |
| 55 | minimally scattering photons |
| 57 | moderately scattering photons |
| 59 | greatly scattering photons |
| 61 | output from intensity calculator 46 |
| 63 | reference time-intensity curve |
| 65 | intensity of minimally scattering photons |
| 67 | intensity of moderately scattering photons |
| 69 | intensity of greatly scattering photons |
| 87 | light-blocking solid rod |
| 93 | time-intensity curve w/central blocking rod |
| 103 | solid rods left of center of light beam |
| 105 | solid rod right of center of light beam |
| 107 | time-intensity curve w/off/center rods |
| 113 | object to be measured |
| 115 | mildly light absorbent layer |
| 117 | highly absorbent core |
| 131 | initial emitter position |
| 133 | initial detector position |
| 135 | initial time-intensity curve |
| 137 | start of narrow measurement window |
| 138 | end of narrow measurement window |
| 139 | numerical result of initial scan |
| 141 | second emitter position |
| 143 | second detector position |
| 144 | region interrupting second scan |
| 145 | second time-intensity curve |
| 149 | numerical result of second scan |
| 151 | third emitter position |
| 153 | third detector position |
| 155 | third time-intensity curve |
| 159 | numerical result of third scan |
| 161 | fourth emitter position |
| 163 | fourth detector position |
| 169 | numerical result of fourth scan |
| 171 | last emitter position |
| 173 | last detector position |
| 179 | numerical result of last scan |

EXAMPLES

The breadth of uses of the resent invention are best understood by example, seven of which are provided below. These examples are by no means intended to be inclusive of all uses and applications of the apparatus, merely to serve as case studies by which a person, skilled in the art, can better appreciate the methods of utilizing, and the power of, such a device.

Example 1

Detection Of Freezing In A Turbid Tissue Model

The detection of freezing, a change in state, in a turbid liquid may be important in the monitoring of materials which must be frozen, such as with biologic samples. It may also be important to be able to detect when freezing has been completed, such as the potential use of an optical device to verify that poultry has been fully frozen, in order to minimize time of freezing before removal from a freezing bath, or that human tissue has been adequately frozen during a procedure known as cryosurgery. The reverse problem may also be important, such as verifying that thawing has started or been completed.

We demonstrated the utility of the present invention to perform such detection in an actual experiment using a gelatin impregnated with light scattering fats, which is an accepted optical model for human tissue. In this experiment (FIG. 1), the probes, emitter 2 and detector 4, were placed upon one surface of cube of sample tissue 5, and thermal plate 6, set to freeze tissue 5, and was placed opposite the probes on tissue 5. As tissue 5 becomes progressively frozen, an ice front will form next to freezing plate 6, and the location of this initial front is marked as interface 8. As time passes, the freezing front will move from interface 8 to interfaces 9, 10, and 11, sequentially.

Photons traveling between emitter 2 and detector 4 take a range of paths through sample 5. When the multiple paths taken by the detected photons are considered, the distribution of paths that the majority of photons take fall inside banana-shaped photon density region 12. Initially, as freezing reaches interfaces 8 and 9, there are no detectable changes in optical path lengths, as no photons from region 12 meet the frozen surface. However, when the freezing front approaches 25 mm from the probes, at interface 10, the farthest traveling photons (those penetrating to the bottom of region 12) begin to pass into, and travel through, the frozen portion of the tissue. Frozen tissue scatters light differently than does unfrozen tissue, so there are changes in the optical paths taken by those photons entering into the frozen region. An increasing number of photons in region 12 enter into the frozen tissue as the interface proceeds to mark 11, which is substantially inside region 12. These optical changes continue until the block is fully frozen, at which time all photons pass through frozen tissue.

Figure 2:
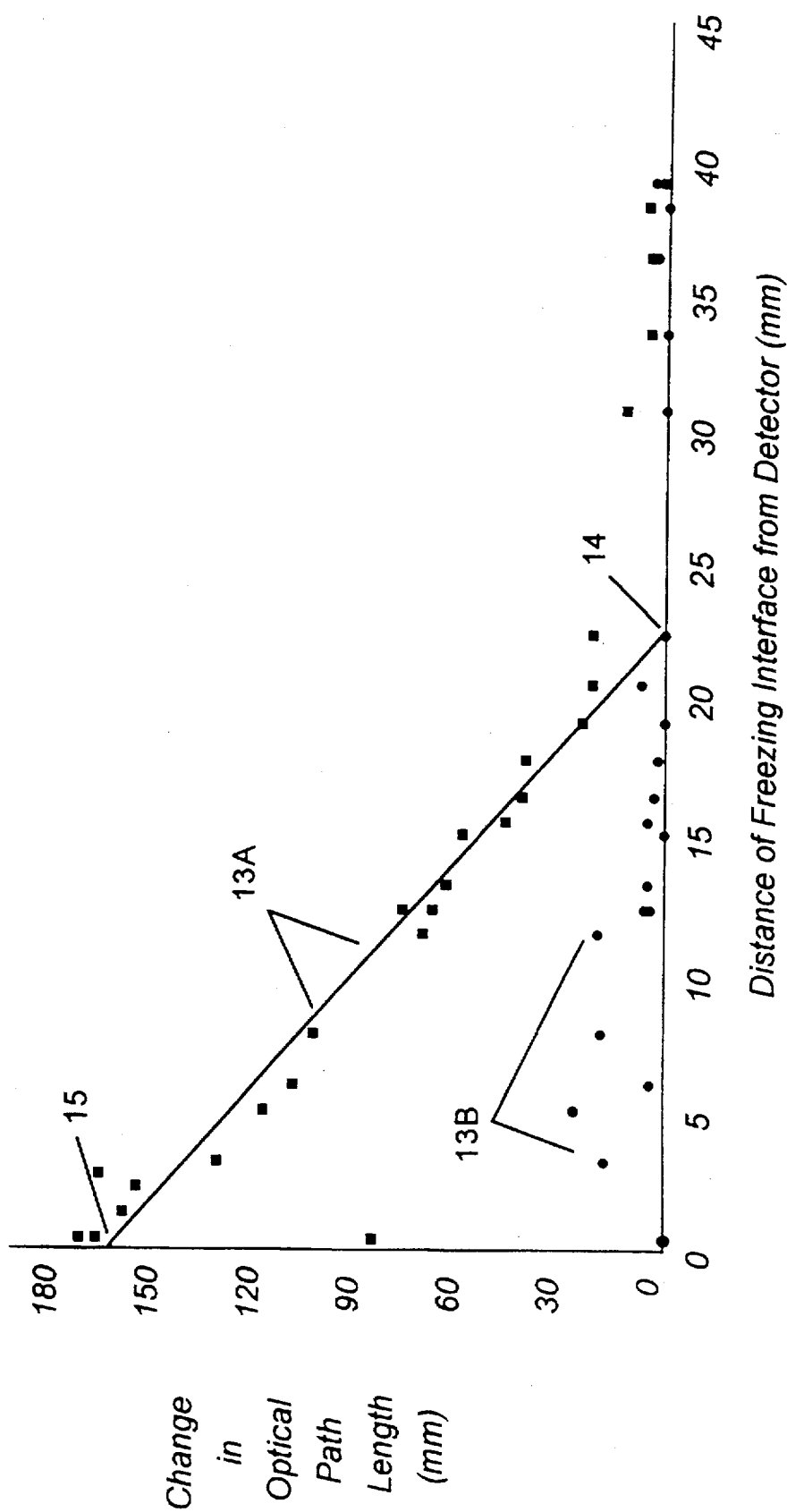
FIG. 2 is a graph of actual optical path length data during a tissue freezing experiment.

The numeric results of this are best understood by studying a graph of optical path length (the distance photons in banana region 12 travel between emission and detection) plotted against freezing interface distance (the distance that the thawing front is away from the emitter and detector), shown in FIG. 2. As long as the thawing depth is farther away than 23 mm from the probes, there is little change in optical path length with changes in freezing depth, shown by mean optical path length curve 13A. As soon as thawing reaches the bottom of region 12 in FIG. 1 (shown at mark 10), there begin to be easily detectable changes in average path length curve 13A as the freezing front continues to move toward the probes (shown at mark 14). Thus, the onset of freezing within region 12 is easily detected with such a method as a change in optical path length. There are much smaller changes, if any, in the optical distance traveled by the earliest detected photons, shown as first detected photon path length 13B. No other method in the prior art would be able to optically detect this process using a similar effect. In addition, the opposite process is also be measurable., That is, thawing can also be detected using a similar system.

EXAMPLES (CONT'D)

Example 2

Localization of Thawing Front in Turbid Solid

In certain types of cancer, treatment is achieved by freezing the tumor using a liquid nitrogen filled needle stuck into the tumor. This allows killing of the tumor without having to cut up tissue in order to remove it. This is important if the tumor is in an critical location in an important organ, such as the brain or liver. However, it can be difficult to detect when the correct amount of freezing has occurred. If too little tumor tissue is frozen, then the tumor lives and the treatment is ineffective; if too much tumor tissue is frozen, then complications may arise due to the injury of healthy tissue and blood vessels through the freezing process. Thus, localization of the extent of freezing, and not only detection of freezing, can be crucial to a patient's health.

We tested the ability of the system described in Example 1, above, to detect and localize such freezing changes. Data are taken from the above example. As above, freezing begins at the bottom of the tissue and works its way toward the probes, emitter 2 and detector 4. A standardization curve can be determined given the following three facts: a) tissue 12 is fully frozen when the freezing front reaches emitter 2 and detector 4, shown at mark 15 in FIG. 2., b) through visual inspection, the freezing front is about 23 mm away from the probes when the optical path length began to change, shown at point 14, and c) in this case, changes in optical path with changes in freezing depth, between the point changes are first detected and the point at which the tissue is fully frozen, are roughly linearly related (though there also does appear to be some nonlinear change at distances between 23 and 40 mm away from the probes, and in many cases such changes will be nonlinear). A calibration curve can now be constructed by fitting a line to the data collected for mean optical path length versus freezing depth. Any measured optical path can now be converted to an estimated depth by finding an optical path length on the Y-axis of a graph such as shown in FIG. 2, and reading the corresponding location of the freezing depth on the X-axis. This measured-path calibration curve would then apply to any similar homogeneous media. Of course, a calibration curve could still be constructed as long as the relationship between path and location of inhomogeneity is known or measurable, even if such relationship were to be nonlinear.

The penetration depth of banana-shaped region 12 is a function of the separation of emitter 2 and detector 4, as shown in FIG. 3. When the probes are moved farther apart, deeper banana-region 16 illuminates deeper into the tissue in deeper, reaching into tissue to depth 17; whereas moving the probes closer makes for a shallow sample region 18 that illuminates tissue only down to depth 19.

Figure 4:
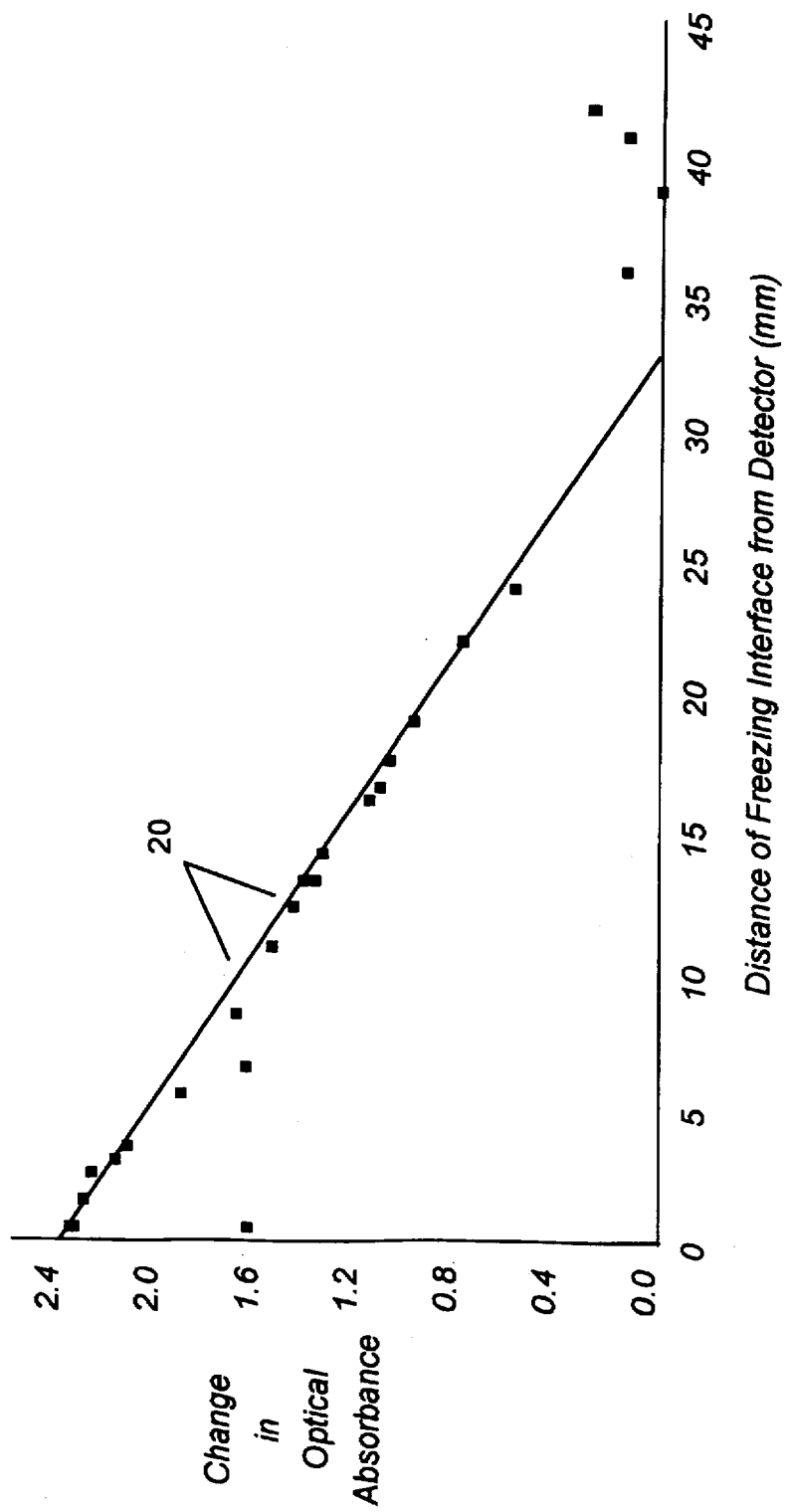
FIG. 4 is a graph of actual optical absorbance obtained during a tissue freezing experiment.

In this experiment, dividing the absorbance of light (log of emitted over detected intensity) by the average optical path length yields a constant. This means that, in this particular case, all of the apparent change in absorption of photons was due to changes in path length ($\Delta A$ is proportional to $\Delta L$), as the absorbance of light (A) is in part a function of the optical distance traveled (L). If all intensity changes are due to path changes alone, then it is possible one could measure in some cases only the intensity of received light, and then infer changes in optical path length from the measured changes in intensity. This is appealing as it is often simpler to perform a measurement of absorbance rather than a measurement of path, in many cases, but it requires that only the optical path, and not other factors, be varying during the measurement process. In the above experiment, plotting change in absorbance alone yields a linear relationship which can then be used as path-effect calibration curve 20, shown in FIG. 4. Path-effect curve 20 in FIG. 4 is analogous to measured-path calibration curve 13A, shown in FIG. 3, only it may be simpler to generate absorbance data than path data. Such stability of factors other than path may not always be present. For example, absorbance can change during freezing, as changes in the absorption spectrum that occur with changes in temperature. In a more complex example than when using gelatin, such as when scanning a breast tumor, or when certain substances freeze, such changes in both path, absorbance, and scattering may all occur, such as when the color of the substance changes such as when blood turns more blue due to a lack of oxygen in the freezing tissue. In this case, measurement of absorbance alone will reflect both path and absorbance changes. However, this does not prevent formation of an image, and the image will simply represent a measure that is a function of path traveled, as well as a function of other parameters. In the case of image formation or tumor detection, such a combined detection of path and absorbance via measured changes in intensity may be sufficient to detect and image a tumor, and the exact mechanism for the change in intensity (absorbance plus scattering inhomogeneities) is not important, only whether the object can be detected or imaged, and whether the image formed is, at least in part, based upon a function of a path effect.

Now that a calibration curve will allow not only detection of the freezing front, but localization of the front as well, such a curve can also be constructed for human tissue. For example, a standard length probe sticking into the tissue could be imaged, and used as an imaging "yardstick" from which depths are judged, or the depth of penetration at which light begins to escape out the other side of a limb may be used to standardize a depth curve.

As each increasing separation of emitter and detector probes a deeper into the medium, as was shown in FIG. 3, multiple depths can be probed by varying the emitter-detector separation. In addition, different areas of the medium can be probed by measuring at different surface locations. This raises advantages for the use of multiple detectors and/or emitters, or for using scanning detectors and/or emitters. Through the use of an array of probes, using a series of emitters and detectors, an image can be formed using a temporal or spatial series of such localizing data. As each increasing separation of emitter and detector probes deeper into the medium, multiple depths can be probed using an emitters and detectors centered upon a specific location, while different regions of the medium can be probed by measuring at different surface locations.

One method of identifying objects based upon a path effect is to calculate a ratio of optical path length to physical separation of emitter and detector. This path ratio is constant within a homogeneous medium (though it may vary near the edges), and such information may be abnormal in the presence of an inhomogeneity. Furthermore, the direction of the deviation (longer or shorter) may yield clues as to the depth of the detected inhomogeneity and its characteristics. This effect of direction of path length deviation occurs because a shallow object obstructs short-traveling photons, increasing average optical path, whereas a deep object obstructs the long traveling photons, decreasing average optical path, both changes compared to a baseline with no object present at all. This "no object" baseline could be determined from normal tissue (for example, the opposite breast for breast tumor imaging), or from nearby normal tissue, or simply from the average characteristics of all tissue measured.

Figure 5:
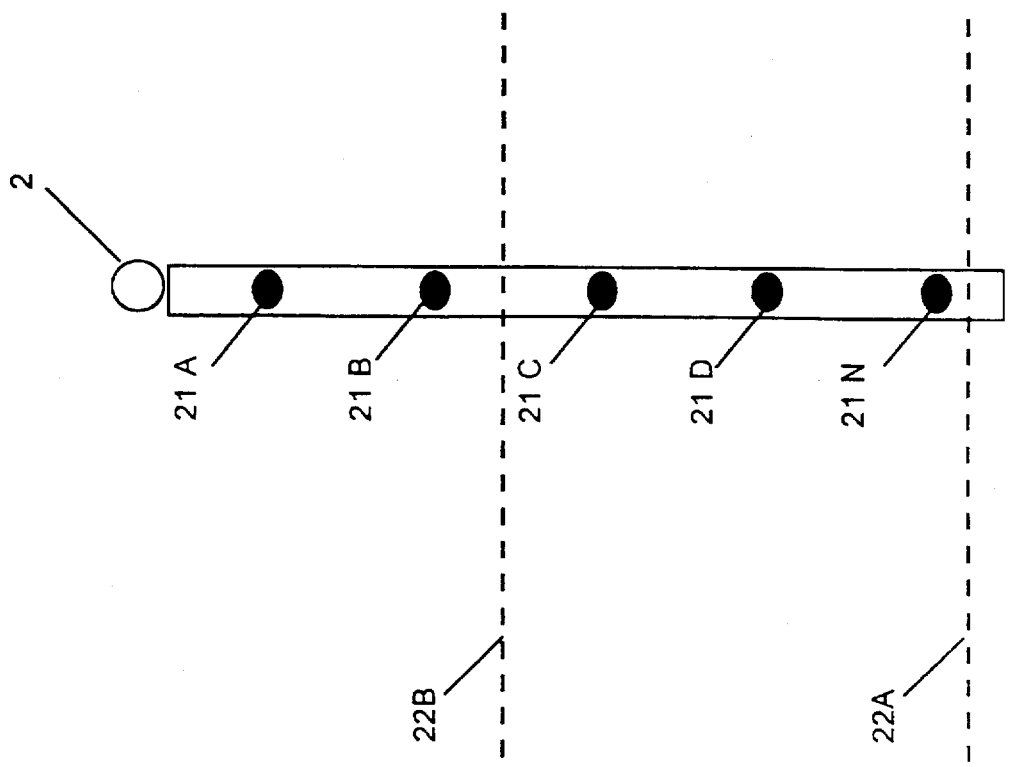
FIGS. 5A and 5B illustrate optical localization of a freezing interface using an intra-tissue needle probe.

One method of using such an array would be to construct a probe shaped like a needle, with emitter 2 at one end, and n multiple detectors 21A through 21N spaced along the length, shown in FIG. 5A where n=5. If such a needle were to be inserted into tissue to be frozen, such that the emitter is buried deep inside the tissue, and freezing begins at the surface and proceeds deeper with time, there would be a change in absorbance and path length, as measured from the emitter to each detector as the freezing front passes by each detector. In FIG. 5A, the deepest portion of the tissue is shown at the top of the illustration, while the skin surface is shown at mark 22A and the freezing interface is shown at mark 22B. Ideal results from such a probe are shown in the table in FIG. 5B. With the freezing interface located at mark 22B, there is no frozen tissue between emitter 2 and detectors 21A and 21B. Thus, the optical average path divided by the physical separation between emitter and detector (path ratio) is constant at 5.00. Once the measurement crosses a freezing interface, however, the path ratio changes from 5.00 to as high as 10.50 in this example, due to scattering changes in the frozen tissue that must be traversed by photons traveling from emitter 2 to detectors 21C, 21D, and 21N. The point at which the path ratio begins to change can be use to localize the freezing interface. Such a probe could also be used to detect tumors or nearby objects using disturbances in this path effect, based upon deviations from an expected or predicted path length.

EXAMPLES (CONT'D)

Example 3

Detection of Changes in the Environment

A simple proximity detector can be constructed from such a system as revealed in example 2, above. Proximity detection, such as the detection of nearby objects in turbid media can be expensive and complicated. The use of the path-effect of a nearby object allows an inexpensive solution.

Figures 6A, 6B, 6C:
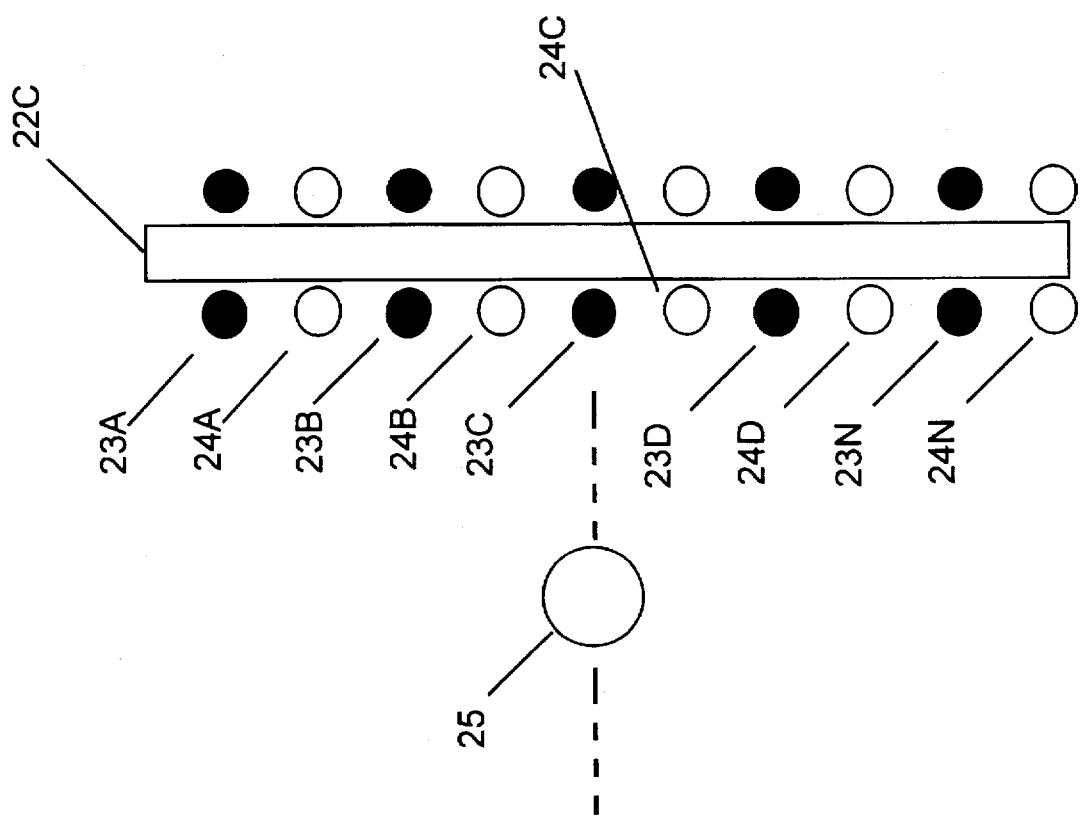
FIGS. 6A, 6B and 6C illustrate optical detection of an object using a probe in turbid water.

In this ideal experiment, capsule shaped object 22C is studded with alternating emitters and detectors (FIG. 6A). At any one time, only one pair of emitters and detectors are on, selected from emitters 23A through 23N and detectors 24A through 24N. All possible pairs of emitters and detectors are, in turn, illuminated and detected. A baseline of average path lengths is thus obtained across multiple detector-emitter pairs. Whenever an object approaches, such as object 25 that moves in an axis perpendicular to the long axis of capsule 22C, heading directly for detector 24C, there will be path changes, as shown in the table in FIG. 6B. These path changes will first appear in widely separated emitter-detector pairs that have a deeply penetrating banana-shaped photon region that touches object 25, but then will appear as well in the more closely-spaced probes, based upon the effect of depth of penetration of the banana-region as shown earlier in FIG. 3. Which pairs are most and least affected, and to what extent, should allow localization, and possibly characterization, of the object. Thus, not only has detection be accomplished, but in addition localization has been achieved. The data could also be computed as path ratios, as shown in the table in FIG. 6C. Using path ratios, the emitter-detector pairs affected by the object are easily seen, as the unaffected pairs in this otherwise homogeneous medium have path ratios of 5.00, while the affected pairs have varied path ratios.

This approach could be used to form an imaging probe that would be located on the surface of skin, yet able to visualize the structure and character of the tissue below it. This could be used as an optical biopsy, characterizing tissue based upon optical properties to distinguish cancer, nerves, blood vessels, plaques on arteries, fat deposits, bleeding, air in tissues, bony growths, swelling, foreign objects, type of fluid in tissues or joints, normal tissue, or other inhomogeneities in tissue from one another.

Example 4

Detection Of Bleeding Or Tumors In Tissue

In medicine, tumors, bleeds in tissue, and other changes constitute changes in the homogeneity of a tissue. Such changes can be detected as changes in the environment in similar manners to the above examples.

Figure 7A:
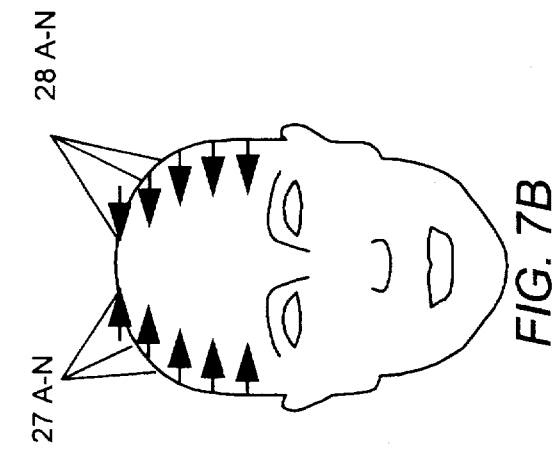
FIGS. 7A, 7B and 7C illustrate an actual experiment detecting and localizing fluid collections in a patient's brain.
Figure 7B:
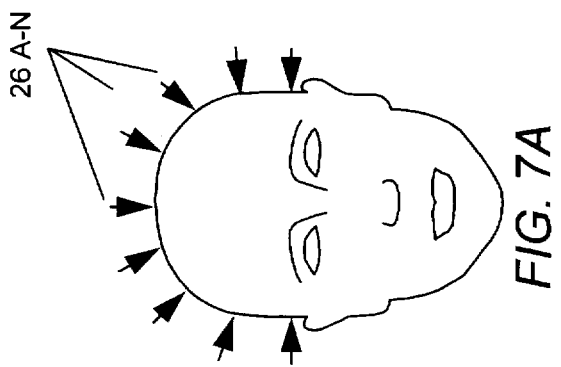
Figure 7C:
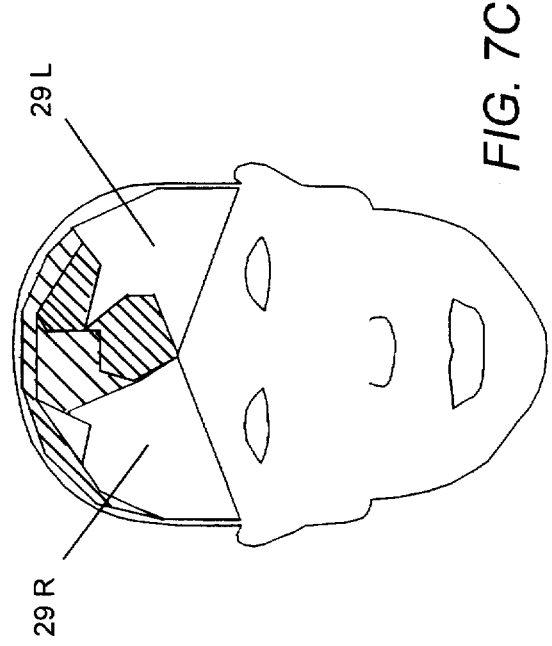

For example, in premature infants, bleeding in the brain leading to excess fluid accumulation and pressure build-up, is a major cause of morbidity and mortality in those infants. We measured path along an infant known to have such excess fluid, with a known collections of fluid lateralized of the left and right sides of the brain, near the ears. The scan was performed by measuring along the top of the infant's head between all pairs of points 26A through 26N, 27A through 27N, and 28A through 28N, in FIGS. 7A and 7B. We then calculated a path ratio, as described in the examples above (optical path divided by the separation of the source and detector), and solved a two-dimensional matrix for the best fit between all of the observed measurements, assuming a linear interpolation (a simplication, but is not essential, and results may be improved by omitting this assumption) for the brain tissue between the points of each measurement. The image, shown in FIG. 7C, obtained from real data, clearly shows as white fluid accumulations 29R and 29L, present within the brain of this infant next to each ear. Such a technique could be used to image superficial and deep tumors, such as those in the breast, and perhaps to measure optical differences between different tissues such as gray and white brain matter, or between normal and disease bra in (such as that with Alzheimer's disease). Preliminary data shows that the optical characteristics of brain with Alzheimer's disease is quite different from normal brain, and this may be detectable noninvasively using such a method. In the case of imaging the brain, the result of the scan shown in FIG. 7 could have been used to guide further medical evaluation or intervention, particularly if the resolution of such a scan can be improved.

Example 5

Detection of End of Freezing

If an emitter and detector pair are placed such that light shines completely through a block of tissue, and the tissue is slowly frozen, path length, and for the most part absorbance, will stop changing once the tissue is completely frozen.

Example 6

Localization of Freezing Point

As tissue or other immobilized liquid/solid mixtures freeze, the ice forming has a unique structure. For example, as a light scattering gelatin freezes, radial ice crystals radiating out from the center of freezing may form. Light traveling along the axis of these crystals, such as if the emitter and detector axis travels through the center of freezing, may undergo changes in absorbance more than changes in scattering as freezing occurs. Conversely, light traveling across the radial ice crystals may find that absorbance changes little as freezing occurs, but that scattering changes markedly. This difference in effect upon photons during freezing, depending upon the angle of the ice crystals taken, can be used as further information to help localize the center or edges of an advancing ice ball in tissue, gelatin, or other scattering media. This effect could be used, for example, to produce a cryosurgery (tissue freezing) probe studded with emitters and detectors, that allows optical imaging of the freezing front directly below the probe as the surgical procedure is in progress. Further, if the object being frozen is a tumor, such as a melanoma, the melanoma may also be visualized, which would allow the surgeon to monitor when the tumor has been fully frozen, or when the freezing front is approaching blood vessels or other structures, or to monitor when the freezing has been irregular and part of the tumor has not yet been frozen.

Example 7

An imaging surgical knife

Based upon the preceeding examples, one could construct a surgical knife, studded with light emitting and detecting fibers. Such a knife would be able to optically image tissue directly under the knife, allowing the surgeon to visualize the tissue and structures about to be cut. If effect, this could allow the surgeon to avoid large blood vessels or nerves, or to better visualize the margins of a tumor during surgery.

DESCRIPTION OF A PREFERRED EMBODIMENT

Figure 8:
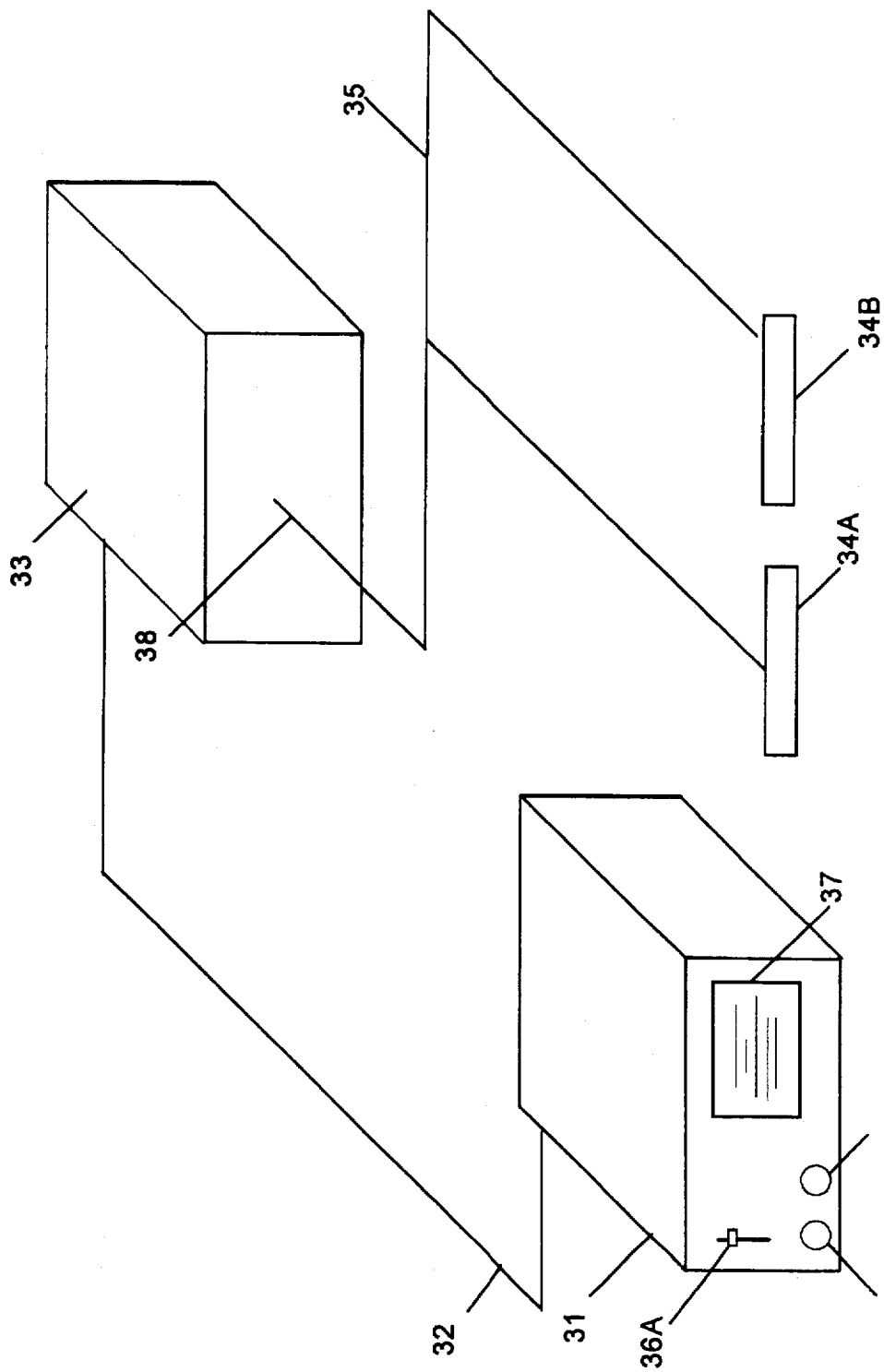
FIG. 8 is a perspective view of a preferred embodiment.

One embodiment of the apparatus will now be described. Referring to FIG. 8, this embodiment consists of control unit 31, connected by cable 32 to remote processor 33, in turn connected to sensor source 34A and sensor detector 34B by cable 35. Power is controlled by switch 36A and adjustment of the device is provided by controls 36B and 36C. A display panel 37, consisting of one or more lines of readout or an image of the distribution of absorbance is on control unit 31. In addition, cable 35 connects to remote processor 33 by way of detachable plug 38, to allow different probes to be used with the same control unit 31 and remote processor 33 pair.

Figure 9:
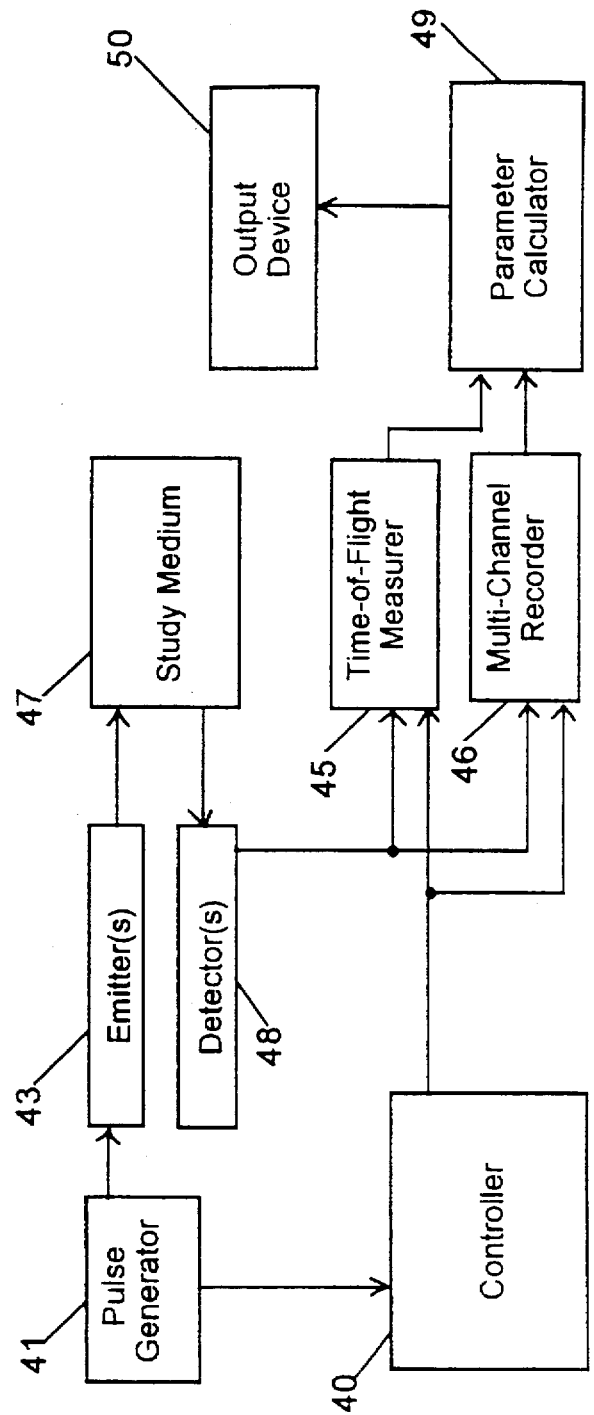
FIG. 9 is a block diagram of the major sections of the spectrophotometer.

In FIG. 9 the workings of the device are revealed in functional blocks. Here, controller 40 sends signals to pulse generator 41, in turn controlling light output from selected light sources in emitter 43. With each pulsed output, controller 40 also sends a timing pulse to time of flight measurer 45 for use in processing detected signals. Signals returning from study medium 47 are picked up by detector unit 48 and sent to measurer 45 and multichannel recorder 46. Time of flight measurer 45 assesses the delay between emission of a light pulse by emitter 43 and the detection of each photon by detector 48. Time of flight information and distribution are stored in multichannel recorder 46, and output to parameter calculator 49 to localize, detect, or form images of the medium and inhomogeneities, which is made available to the user on output device 50.

Methods of determining absorbance, derived from intensity or photon counting, and path lengths, derived from window gating, are multiple, but fall within the scope of this invention if used for the determination of a path effect for the purpose of calculating a spatial distribution of inhomogeneities within a medium that scatters radiative waves. In this embodiment, path lengths are estimated by directly measuring the time of flight through the study medium of each photon, but the effect can be achieved using an optical gate, modulated light signals, sound waves, pressure waves, or other types of radiative waves that exhibit path effects, which can then be used to measure and characterize inhomogeneities and the medium.

TYPICAL WAVEFORMS DURING OPERATION OF THE DEVICE

Operation of the device can be illuminated more fully by studying typical waveforms encountered during data acquisition. These 'typical' waveforms were taken from actual data obtained using one embodiment of the device. These waveforms are provided as examples only, and no limitation of design or operation of the device by the specific patterns discussed below is implied or intended.

Figure 10:
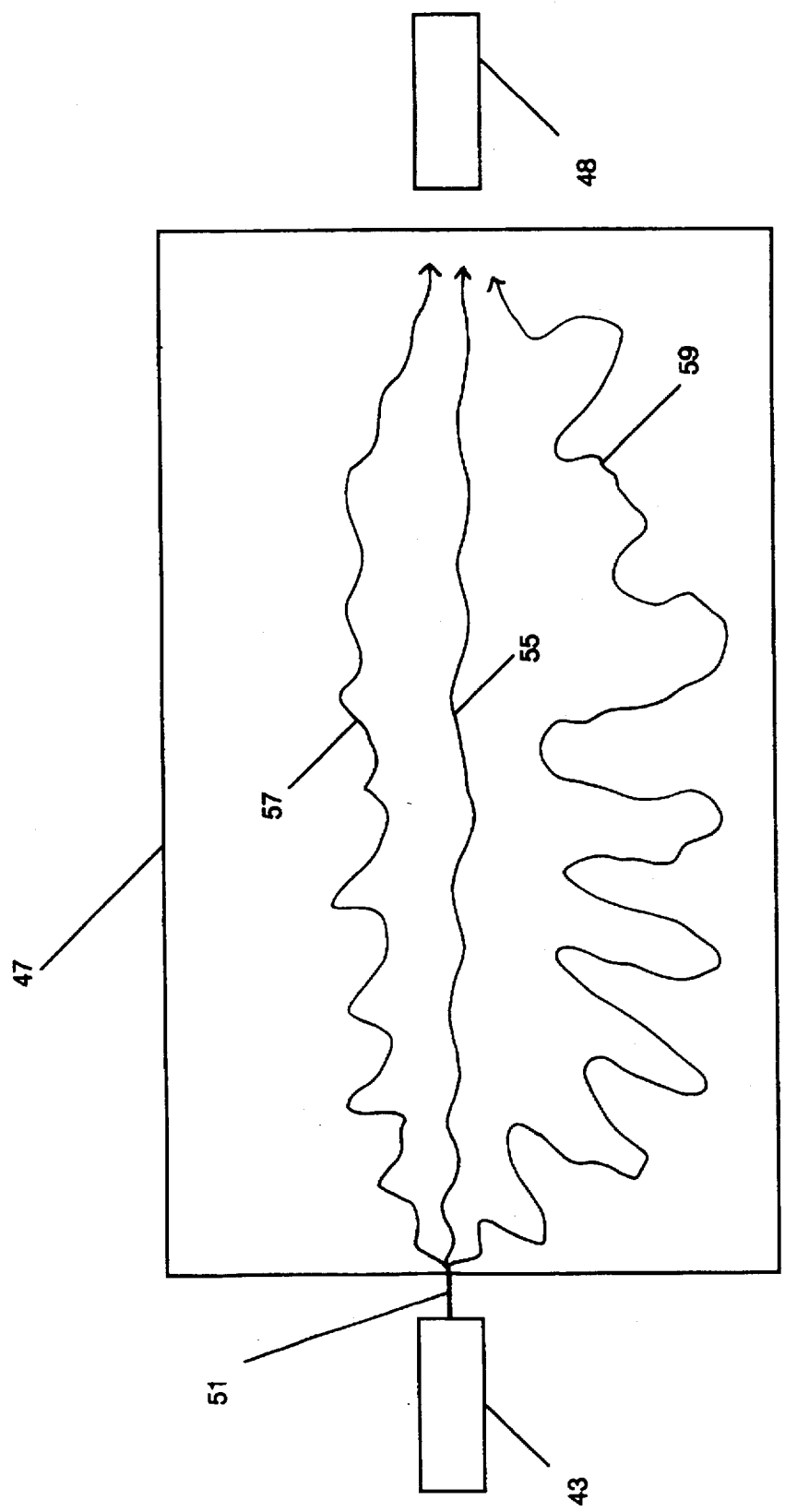
FIG. 10 illustrates the effect of scattering of light.

Of note, in the photon transit diagrams representing photon travel through the medium in FIGS. 10–12, photon movement is shown from left to right, and upward or downward deviation of the photons is representative of scattering. For graphs of photon intensity versus time in FIGS. 11–13, time is always shown on the x-axis and instantaneous intensity is shown on the y-axis, but neither axis is shown to scale as compression or expansion of each axis has been performed where needed for purpose of clarity.

The effect of scattering upon a pulse of light is shown in FIG. 10. Here, emitter 43 emits a pulse of photons 51 into study medium 47. Scattering lengthens the distance traveled by photons between emitter 43 and detector 48, and thus delays arrival of the photons at the detector. Minimally scattering photons 55 travel the most direct line between emitter 43 and detector 48, and thus arrive first, while other photons scatter moderately 57 or greatly 59, and thus arrive later. Most of the initial pulse of photons 51 scatter moderately, and these photons arrive at detector 48 after the minimally scattering photons have arrived, but before the greatly scattering photons do so.

Now that the effect of scattering is understood, the basis of the use of optical path length for object detection can be demonstrated (FIGS. 11A–11F). As opposed to the use of scattered signals returning to a detector nearby to the emitter, the following examples, for purposes of contrast, will show the use of a transmission geometry in which the emitter and detector are located 180 degrees opposite one another. Both methods, the "nearby" and the "transmission" geometries, have their own advantages, and either configuration can be used in path-based imaging.

In this example, shown in FIG. 11, the top figures (FIGS. 11A, 11C, and 11E) are similar to FIG. 10, and show the passage of a group of photons through a study medium over time, while the lower figures (FIGS. 11B, 11D, and 11F) show the voltage at output 61 from detector 48 at the same instant in time as the figure above. In FIG. 11A, photon pulse 51, consisting of a group of photons all emitted from emitter 43 at about the same instant, has already traveled into medium 47. Minimally scattering photons 55 have passed entirely through the medium, and are arriving at detector 48. Moderately scattering photons 57 and greatly scattering photons 59 are all still traveling through the medium, as they have taken a longer route due to increased scattering. In FIG. 11B, output 61 of detector 48 is shown at the same time point as FIG. 11A. Output 61 is non-zero and rising, reflecting the arrival of minimally scattering photons 55 at detector 48. Moderately-scattering photons 57 and greatly-scattering photons 59 are still en route to the detector, and thus have not registered at this time. In FIGS. 11A and 11B only minimally scattering photons have had enough time to reach detector 48, whereas in FIG. 11C more time has elapsed such that moderately scattering photons 57 are now arriving at detector 48. Greatly scattering photons 59 still have not yet reached detector 48. FIG. 11D shows that output 61 of detector 48 is now maximized. This is because the most of the photons from pulse 51 scatter moderately. In FIG. 11E, yet more time has passed, and greatly-scattering photons 59 are now finally arriving at detector 48. In FIG. 11F, the intensity reflects the greatly scattering photons.

Time-intensity curve 63 represents the intensity of light at detector 48 over time in the absence of any object placed between emitter and detector, and will be referred to as reference time-intensity curve 63. Different portions of reference curve 63 represent photons with different amounts of scattering. The left-most portion of the curve represents intensity of minimally scattering photons 65; the middle portion represents intensity of moderately scattering photons 67; the right-most region represents intensity of greatly scattering photons 69. Thus, the earliest detected photons in reference waveform 63 have traveled the least far, while the latest detected photons have traveled the furthest of all. In practice, there is no clear division between groups of photons with different amounts of scattering, but this continuous function has been simplified for the purpose of illustration into three groups (minimally scattering 65, moderately scattering 67, and greatly scattering 69) for the purpose of illustration.

The shape of the time-intensity curve, a reflection of when photons arrive at detector 48, can be modified by material through which the light passes (FIGS. 12A–12F). In FIG. 12A, light-blocking solid rod 87 has been placed such that it blocks the direct path between source 43 and detector 48. Minimally scattering photons 55 are completely stopped by rod 87, while moderately scattering 57 and greatly scattering 59 photons pass unimpeded by traveling around the rod. In FIG. 12B, this shows up at then output of detector 48 as time-intensity curve 93, which is flattened in the early part as compared to reference wave 63. FIG. 12C, representing the same event as in FIG. 12A after additional time has passed, shows both moderately scattering photons 57 and greatly scattering photons 59 arriving normally at the detector, and thus the last half of time-intensity curve 91 is very similar to reference wave 63. When time-intensity curve 93 is studied in FIG. 12D, intensity of minimally scattering photons 65 is much less than in reference curve 63, while intensity of the moderately-scattering 67 and greatly scattering photons 69 are the same for both curves.

This result may be contrasted with FIG. 12E, in which two pairs of light-blocking rods, rods 103 and 105, are placed on either side of the direct path between source 43 and detector 48. Here, minimally scattering photons 55 are not blocked, whereas moderately scattering photons 57 and greatly scattering photons 59 are now completely blocked by the rods. FIG. 12F shows the effect of rods 103 and 105 on dual-blocked time-intensity curve 107, as compared to reference waveform 63. Intensity of minimally scattered photons 65 is the same for both reference and rod-blocked waveforms, whereas intensity of moderately scattering photons 67 and greatly scattering photons 69 is reduced in curve 107 compared to reference curve 63.

Figure 13:
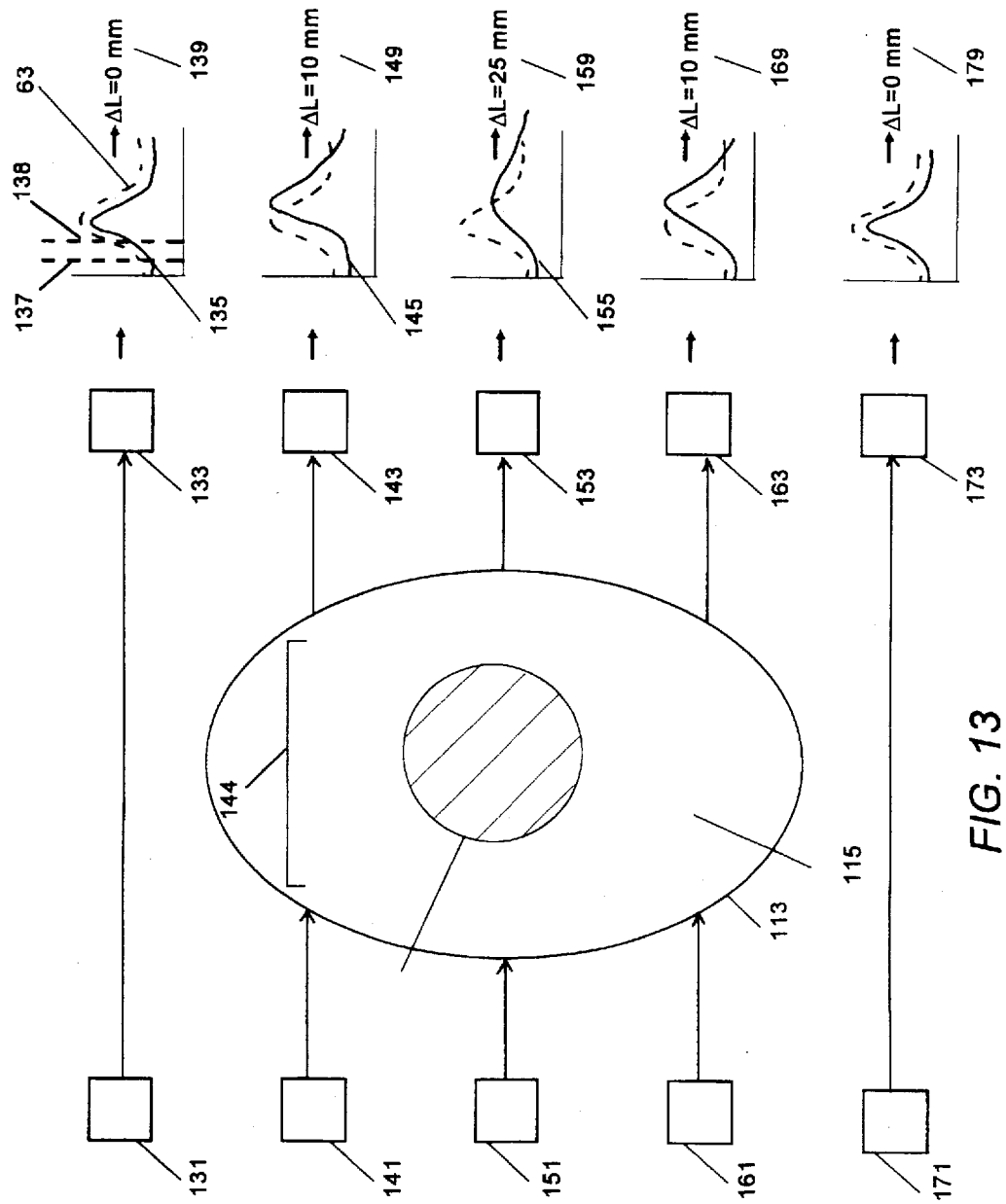
FIG. 13 illustrates a one dimensional scan of a turbid medium.

Multiple time-intensity curves may be obtained from a single object as a first step toward making an image. In FIG. 13, time-intensity curves are measured at five locations on object 113. Object 113 consists of mildly absorbent outside layer 115 surrounding highly scattering and absorbent core 117. In the first measurement, emitter 43 is positioned at 131 and detector 48 is positioned at 133. The result is time-intensity curve 135, which is compared to reference curve 63 (shown as a dashed line). A narrow measurement window is defined as the interval between time marks 137 and 138. This narrow window restricts optical path length measurement (in this example) to the early portion of the time-intensity curve, the portion that represents the arrival of the first 1% of the detected photons, which is primarily composed of minimally scattering photons 65. Calculating a change in optical path ($\Delta L$) of the earliest detected 1% of photons in sample curve 135 compared to reference 63 yields result 139, which in this case, is $\Delta L=0$ mm. This result indicates that the early photons in sample curve 135 travel, on average, the same distance as they did in reference curve 63 when the sample was not present. This makes sense, as the sample does not fall directly upon the emitter-detector axis, and thus would not be expected to have an effect on early photon arrival time. However, the scattering is probably great enough that there may be an effect upon average photon optical distance even at this emitter-detector position, and is likely to be an even greater effect upon the average path traveled by the late-arriving highly-scattered photons. This effect on late photons occurs even when the object is off of the emitter-detector axis as the late arriving photons are highly scattered photons, likely to have diverged well off of the emitter-detector axis and encountered object 113, even though the object is not directly on the emitter-detector axis. This effect of encountering an off-axis object by the highly scattering photons can be used as a part of an imaging function.

TYPICAL WAVEFORMS DURING OPERATION OF THE DEVICE (CONT'D)

In the second measurement, emitter 43 is moved to position 141, and detector 48 is moved to position 143. Region 115 of object 113 now interrupts the direct travel between emitter 43 and detector 48, shown at 144. Comparison of sample curve 145 to reference curve 63 yields result 149, in this case is $\Delta L=10$ mm, indicating that minimally scattering photons are now traveling, on average, 10 mm farther between emitter and detector in region 115 of object 113 than they did in the absence of the object. Similarly, placing emitter 43 at 151 and detector 48 at 153 yields sample time-intensity curve 155, and result 159, in this case is $\Delta L=25$ mm, indicating that minimally scattering photons are now traveling, on average, 25 mm farther than before. A fourth scan at 161 and 163 yields result 169, while a final scan at 171 and 173 yields result 179.

Figure 14:
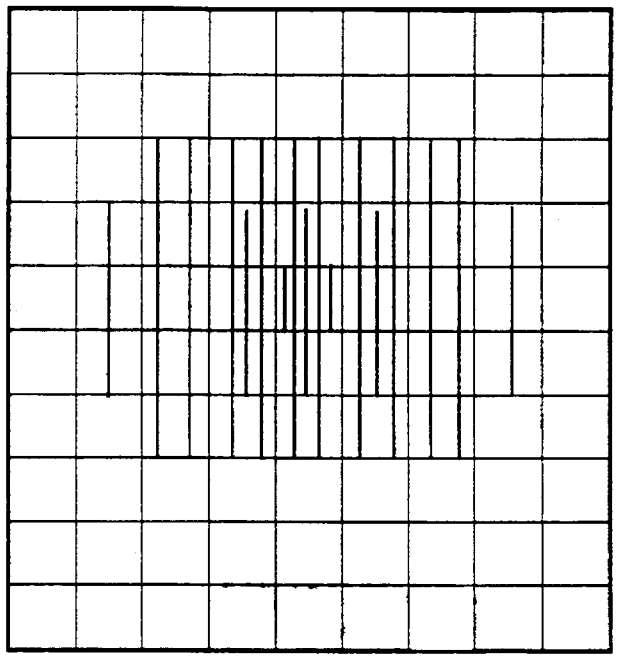
FIGS. 14A and 14B illustrate the formation of an image using data from a two-dimensional scan of a turbid medium.

Instead of measuring one row of locations, as was illustrated in FIG. 13, an object may be scanned in two or more dimensions. A two-dimensional scan of object 113 could yield the data table of early photon optical path lengths shown in FIG. 14A. This data table would represent the change in optical path length for the early arriving photons, compared to a reference, and would be measured at multiple locations in two dimensions. Increasing the number of columns and rows measured improves resolution, while graphing the results, as shown in FIG. 14B, facilitates interpretation of the image.

This technique can easily be extended to three dimensions, using multiple axes of scanning and the effect of emitter-detector separation to influence measurement depth, to allow tomographic imaging. The resulting image can be related to the distribution of absorbance, concentration, scattering, or other features of the study medium. The length of the photon path traveled by certain groups of photons, such as the early photons, could serve as the basis for the image.

If all photons had been measured, rather than measuring only photons within a narrow time window, it would be difficult to identify through what region of object 113 photons had passed. Limiting the time window to measure only the minimally scattering photons insures that only photons that have passed through a region directly between an emitter and a detector are measured. For some types of images, however, combinations of regions may be used in the result calculation. In addition, the scan can use different patterns of measurement (e.g., moving detector and emitter in a circle as opposed to a line), to allow tomographic imaging. Next, emitter and detector do not need to be on opposite sides of a subject. Furthermore, use of an optical shutter, to divide light into time-constrained components falls within the spirit of this invention. Lastly, modification of the measurement to introduce other methods of time-constraining the signal, such as interferometry, all fall within the spirit of the device, if used in a combination to measure or select data indicative of path of travel.

For example, an amplitude-modulated signal could be introduced into the sample. As different path lengths would cause the propagating radiative signal to arrive at different times, the detected wave would be offset in time by some amount. This offset, a representation of some averaging function of all courses taken by the radiative wave, could be deduced by timing the offset of the wave. One method to do so is to measure the phase angle of the radiative wave, the offset in terms of degrees or radians, that the wave has been delayed. Knowing the delay angle, called the angle of phase delay or angular phase of the signal, and knowing both the modulation frequency and the speed of radiative wave travel in the medium, the time of offset may be calculated and converted into distance traveled. Such modulated waves may also be added and subtracted. For example, if two radiative waves from two emitters are set out of phase, say by 180 degrees, then the difference between the radiative waves at each source shall be 180 degrees. However, in between these emitters, as one travels from one emitter to the other, there will be a shift in phase by 180 degrees in the detected signal. Of course, there will be a background (DC) component consisting of highly scattered light, but there will also be a modulated (AC) component that will vary, and the phase of this modulated component will shift 180 degrees as one travels from one emitter to the other. One can arbitrarily select a phase threshold, such as the null-phase threshold at which the phase is exactly 90 degrees offset from each emitter, and monitor the location of this threshold. This null phase line, or any other phase line (such as the 45 degree phase line), can be used as a path effect function in order to estimate the location of inhomogeneities in the medium. The modulated signal could also be frequency-modulated, as different frequencies of modulation would allow different structural information to be assessed, similar to the use of varying frequencies in radar or in ultrasound in order to gain additional structural information.

The use of the detection of the optical path length of the early photons is described, but many other effects can be used, including, but not limited the distribution of photon distances traveled, mean photon distance traveled, distribution of photon transit time through the medium, mean photon transit time through the medium, time of first detected photons, ratio of optical path length to physical path length, apparent absorbance, transmission, coherence, optical rotation, turbidity, and diffusivity, modulation phase angle, delay of first detected photons, and time of ballistic echo. In each of these cases, we can define a detection algorithm $P(x,y,z,t)$, which is the probability that an object exists at location $(x,y,z)$ in space at time $t$. This algorithm $P$, which will be used to perform detection or imaging, may be considered a function of the measured path effect $F(x,y,z,t)$, as well as of other factors $G(x,y,z,t)$. As long as $P$ is in some manner a function of path effect $F$, then a calibration algorithm may be written, just as was done in the preceeding examples, and used to determine the presence, location, or structure of an inhomogeneity. Of course, the device or method used must provide the necessary structure or steps to perform such measurements, thus allowing the image or detection to be performed. In fact, the solution used in imaging may not even be remotely mathematical in nature (for example, the solution could be achieved structurally), and the equational description above is provided simply for illustrative purposes of the fact that whatever physical property is measured, that this property should be at least a function of path effect; however, the use of such equations is not intended in any way to indicate that the method and apparatus described are reducible to structureless mathematical functions.

Many quantifiable parameters can be measured. In this case, the detection and localization of an inhomogeneity have been disclosed. However, the presence, location, or structure of an inhomogeneity can be disclosed to the user by presenting the data in an interpretable form, including but not limited to, presence, spatial location, radial direction, radial distance, shape, distribution, number, depth, distance, structure, absorbance, scattering coefficient, modified scattering coefficient, anisotropy factor, and coefficient of absorbance of at least one inhomogeneity. Absorbance is a function specified by Beer's Law, where absorbance (A), related to the log of the ratio of intensity of the emitted signal divided by the intensity of the detected signal, is equal to a constant (called the extinction coefficient, $\epsilon$, which is known for many substances or can be measured) times the concentration of the substance (C) times the optical path length (L). Beer's law is not well suited to highly scattering media. In scattering substances, the intensity of the detected light falls off as the intensity of the emitted light times e to a negative number, with that number proportional to $\mu a+(1-g)*\mu s$. Mu with the 'a' subscript is the coefficient of absorbance, while mu with an 's' subscript is the coefficient of scattering. The effective, or apparent, scattering in tissue is related to the anisotropy constant 'g' that corrects for the tendency of photons to travel in a forward direction in tissue after scattering. Each of these numbers can be determined and used as an imaging variable. For example, it is known that different kinds of tissue, such as tumors, have different optical properties than other kinds of tissue, and the above factors may each vary between different types of tissue, or between different media.

Another modification is to use the collection of multiple samples over time. Repeated measures can help average out noise in a sample measurement, and thus help give improved accuracy. In biological systems, or in the detection of nearby objects, the use of multiple measurements can allow changes in the medium to be detected. For example, while imaging of the nearby medium may be complex, the detection of changes in the medium may prove a simpler calculation. Thus, changes in the calculated values can be used to identify changes in the nearby medium, or to allow cancellation of unknowns by determining the net change in a measured parameter. An example of the latter effect would be the determination of change in absorbance (ΔA) in a system in which this change will allow calculation of a change in concentration (ΔC) using a Beer's Law approximation. In this case, it may not be important what the starting conditions are, only the a change has occurred. Lastly, the collection of multiple samples over space may allow better image formation by allowing measurement of the medium at multiple locations.

The measurements made with such a device can be made more accurate if corrections are made given information known about the medium. For example, in the method of imaging demonstrated in FIG. 13, the known reference path length can be used to determine the zero point for ΔL. Or, in computing concentrations of substances in the human body, a known measurement of some known concentration may allow fine-tuning of the estimate, such that all recorded changes could be computed in absolute terms, rather than in relative terms.

The device as described is capable of measuring the spatial distribution of light absorbing or other radiation absorbing substances contained in a radiation scattering media. However, in the broad sense, the device as disclosed should be able to operate using any radiative wave in a wave scattering medium. The technology cited in this embodiment is currently available to construct this device inexpensively, to make the device portable, and to have it operate in real time. Furthermore, construction and methods of this device are unique, distinct from other spectrophotometers in the art. Multiple, significant advantages of this design are inherent from an incorporation of both time of flight and absorbance measurements.

Various additional modifications may be made within the spirit of this invention by those skilled in the art, and no undue limitation is to be implied of inferred from an omission of these items from the above description, and in the following disclosure. While the above disclosure has described one embodiment, it will apparent to those skilled in the art that various changes and modifications may be made therein, without departing from the spirit of the present invention. It is therefore stated that such changes and modifications all fall within the true spirit and scope of the present invention.

I have discovered an improved apparatus and method that measures a path effect (such as from using either temporally modulated light sources or intensity quantitated light sources), using multiple discrete or continually varying wavelength radiative sources, that allows the detection, localization, and characterization of inhomogeneities in a radiation scattering environment. The device has been built and tested in several configurations, and has immediate application to several important problems, both medical and industrial, and thus constitutes an important advance in the art.

We claim:

1. An improved spectrophotometer for monitoring at least one inhomogeneity in a turbid medium, comprising:
  (a) source means for illuminating said medium with electromagnetic radiation of at least one wavelength;
  (b) detector means for detecting at least a portion of said illuminating radiation after it has propagated through said medium, said detected portion including at least one wavelength if said illuminating radiation, said detector means also providing output signals, said output signals being comprised of multiple regional component signals, each of said regional component signals comprised of detected radiation having propagated through a different region of the medium;
  (c) path resolution means for receiving said output signals and for measuring an optical path effect on said output signals by said at least one regional inhomogeneity, and for providing a path influenced signal, said optical path effect being at least partially a function of the substantially non-parallel multiple courses through said medium taken by said illuminating radiation between said illumination and said detection; and,
  (d) regional quantitation means for receiving the path influenced signal, for resolving at least one of said multiple regional component signals, and for determining at least one quantifiable parameter affected by said at least one regional inhomogeneity in the medium based upon at least one of said resolved regional component signals.

2. The spectrophotometer of claim 1, wherein:
  (a) said source means further includes variation means for producing temporally varying electromagnetic radiation of at least one wavelength; and,
  (b) said path resolution means further includes delay measurement means for measuring a function of a radiation propagation delay distribution, said distribution corresponding to a distribution of times required for radiation to traverse said medium between said illumination and said detection, said function representing at least a part of all information contained in said delay distribution.

3. The spectrophotometer of claim 2, wherein:
  (a) said variation means includes pulse means for producing brief, discontinuous pulses of radiation; and,
  (b) said delay measurement means includes means for detection of photons arriving over at least one narrow range of propagation delays, each said narrow range of delays corresponding to a narrow range of times of flight taken by said photons through the medium.

4. The spectrophotometer of claim 2, wherein:
  (a) said variation means includes intensity modulation means for providing amplitude modulation of source intensity; and,
  (b) said delay measurement means includes means for determining an effect of propagation delay through the medium based upon the angular phase of said detected signal.

5. The spectrophotometer of claim 4, wherein said means for resolving paths includes means to estimate a function of path lengths through said medium based upon said angular phase.

6. The spectrophotometer of claim 2, wherein said effect of optical path is selected from the group consisting of distribution of photon distances traveled, mean photon distance traveled, distribution of photon transit time through the medium, mean photon transit time through the medium, time of first detected photons, ratio of optical path length to physical path length, apparent absorbance, transmission, coherence, optical rotation, turbidity, and diffusivity, modulation phase angle, delay of first detected photons, and time of ballistic echo.

7. The spectrophotometer of claim 1, wherein said quantifiable parameter is a characterization of tissue by normal tissue type, said tissue type is selected from the group consisting of nerves, blood vessels, fat deposits, and other normal macroscopic inhomogeneities in tissue.

8. The spectrophotometer of claim 1, wherein
   (a) said detector means further includes intensity measurement means for measuring an intensity of said detected electromagnetic radiation at said at least one wavelength; and,
   (b) said path resolution means further includes apparent absorbance computation means for estimating a path effect based upon spatial and temporal changes in measured intensity.

9. The spectrophotometer of claim 8, wherein said effect of optical path is selected from the group consisting of distribution of photon distances traveled, mean photon distance traveled, distribution of photon transit time through the medium, mean photon transit time through the medium, time of first detected photons, ratio of optical path length to physical path length, apparent absorbance, transmission, coherence, optical rotation, turbidity, and diffusivity, modulation phase angle, delay of first detected photons, and time of ballistic echo.

10. The spectrophotometer of claim 1, wherein said quantifiable parameter is a characterization of tissue by tissue state, said tissue state is selected from the group consisting of frozen, thawed, heated, living and dead.

11. A method for noninvasively detecting at least one regional inhomogeneity in a turbid medium, comprising:
    (a) illuminating said medium with electromagnetic radiation of at least one wavelength;
    (b) detecting at least a portion of said illuminating radiation after said radiation has propagated through said medium over multiple non-parallel paths, and for providing output signals, said output signals being comprised of multiple regional component signals, said component signals detected after propagating through different regions of the medium;
    (c) measuring at least one optical path effect on said output signals by said regional inhomogeneity, said optical path effect influenced by the presence of said at least one regional inhomogeneity;
    (d) resolving at least one of said multiple regional component signals; and,
    (e) determining from said measured path effect, at least one quantifiable parameter influenced by said at least one regional inhomogeneity in the medium based upon at least one of said regional component signals.

12. The method of claim 11, wherein:
    (a) said step of illuminating the medium further includes the step of generating temporally varying electromagnetic radiation of at least one wavelength; and,
    (b) said step of measuring a path effect further includes the step of measuring a function of a radiation propagation delay distribution, said distribution corresponding to a distribution of times required for radiation to traverse said medium between said illumination and said detection, said function representing at least a part of all information contained in said delay distribution.

13. The method of claim 12, wherein the step of generating temporally varying electromagnetic radiation further includes the steps of:
    (a) producing brief, discontinuous pulses of radiation; and,
    (b) said step of measuring a function of the delay includes the step of detecting photons arriving over at least one narrow range of propagation delays, each said narrow range of delays corresponding to a narrow range of times of flight taken by said photons through the medium.

14. The method of claim 12, wherein:
    (a) the step of illumination further includes the step of modulating the intensity of said source; and,
    (b) the step of measuring a function of the delay includes the step of determining a propagation delay though the medium based upon the angular phase of said detected signal.

15. An apparatus for detecting at least one region of inhomogeneity in a medium that scatters a radiative wave, comprising:
    (a) source means for emitting said radiative wave into said medium;
    (b) detector means for detecting at least a portion of said emitted radiative wave after a propagated through said medium and for generating output signals, said output signals being comprised of multiple regional component signals, each of said regional component signals comprised of detected radiation having propagated through a different region of the medium;
    (c) path resolution means for receiving said output signals and for measuring an optical path effect on said output signals by said at least one region of inhomogeneity and providing resolved signals, said optical path effect being at least partially a function of the substantially non-parallel multiple courses through said medium taken by said detected portion of the emitted wave between emission and detection;
    (d) regional quantitation means for receiving the resolved signals, and for determining at least one quantifiable parameter affected by said at least one regional inhomogeneity in the medium based upon at least one of said regional component signals.

16. An improved medical instrument for identification in a living body of at least one unknown tissue by tissue type, comprising:
    (a) means for illumination of at least a portion of said living body with electromagnetic radiation;
    (b) detector means for detecting portions of scattered illuminating radiation having propagated through said at least a portion of said living body, and for providing output signals;
    (c) quantification means for receiving said output signals, said received signal being comprised of multiple regional component signals, each of said regional component signals comprised of detected radiation having propagated through a different region of the living body, and for determining at least one quantifiable parameter affected by said at least one unknown tissue based upon at least one of said regional component signals; and,
    (d) classification means for classifying at least one of said at least one unknown tissue by tissue type, where said tissue type is selected from the group consisting of nerve, blood vessel, bleeding in tissue, tumor, and other tissue types in accordance with at least one of said at least one quantified parameter.

17. A method of monitoring a change in state within a turbid medium, said method comprising the steps of:
    (a) illuminating said medium with electromagnetic radiation;

(b) detecting portions of said illuminating radiation having propagated through said medium, said detected portions comprised of multiple regional component signals, each of said component signals comprised of detected radiation having propagated through a different region of the medium;

(c) measuring at least one optical path effect based upon said detected portions of the illuminating radiation, said optical path effect being at least partially a function of the substantially non-parallel multiple courses through said medium taken by said illuminating radiation between said illumination and detection, and influenced by said change of state; and, (d) characterizing, based upon said measurement of at least one optical path effect, at least one changing region of said medium based upon at least one of said multiple regional component signals.

* * * * *